(12) United States Patent
Reardan et al.

(10) Patent No.: US 8,731,963 B1
(45) Date of Patent: *May 20, 2014

(54) SENSITIVE DRUG DISTRIBUTION SYSTEM AND METHOD

(75) Inventors: Dayton T. Reardan, Shorewood, MN (US); Patti A. Engel, Eagan, MN (US); Bob Gagne, St. Paul, MN (US)

(73) Assignee: Jazz Pharmaceuticals, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/592,202

(22) Filed: Aug. 22, 2012

Related U.S. Application Data

(63) Continuation of application No. 13/013,680, filed on Jan. 25, 2011, now abandoned, which is a continuation of application No. 12/704,097, filed on Feb. 11, 2010, now Pat. No. 7,895,059, which is a continuation of application No. 10/322,348, filed on Dec. 17, 2002, now Pat. No. 7,668,730.

(51) Int. Cl.
*G06Q 10/00* (2012.01)

(52) U.S. Cl.
USPC .................................. 705/2; 705/3; 707/803

(58) Field of Classification Search
USPC ......................................... 707/803; 705/2, 3
See application file for complete search history.

(56) References Cited

U.S. PATENT DOCUMENTS

| | | | |
|---|---|---|---|
| 3,556,342 A | 1/1971 | Guarr | |
| 4,847,764 A | 7/1989 | Halvorson | |
| 4,976,351 A | 12/1990 | Mangini et al. | |
| 5,737,539 A | 4/1998 | Edelson et al. | |
| 5,845,255 A | 12/1998 | Mayaud | |
| 5,924,074 A | 7/1999 | Evans | |
| 5,963,919 A * | 10/1999 | Brinkley et al. | 705/28 |
| 6,021,392 A | 2/2000 | Lester et al. | |
| 6,045,501 A | 4/2000 | Elsayed et al. | |
| 6,055,507 A | 4/2000 | Cunningham | |
| 6,112,182 A | 8/2000 | Akers et al. | |
| 6,315,720 B1 | 11/2001 | Williams et al. | |
| 6,347,329 B1 | 2/2002 | Evans | |
| 6,564,121 B1 | 5/2003 | Wallace et al. | |
| 6,687,676 B1 | 2/2004 | Denny | |

(Continued)

FOREIGN PATENT DOCUMENTS

EP  0527027 A1  2/1993

OTHER PUBLICATIONS

"Advisory Committee Video on Xyrem, Oral Solution", (May 29, 2001), 9 minutes, 8 seconds.

(Continued)

*Primary Examiner* — Lena Najarian
(74) *Attorney, Agent, or Firm* — Schwegman Lundberg & Woessner, P.A.

(57) ABSTRACT

A drug distribution system and method utilizes a central pharmacy and database to track all prescriptions for a sensitive drug. Information is kept in the database regarding all physicians allowed to prescribe the sensitive drug, and all patients receiving the drug. Abuses are identified by monitoring data in the database for prescription patterns by physicians and prescriptions obtained by patients. Further verification is made that the physician is eligible to prescribe the drug by consulting a separate database, and optionally whether any actions are taken against the physician. Multiple controls beyond those for normal drugs are imposed on the distribution depending on the sensitivity of the drug.

28 Claims, 16 Drawing Sheets

(56) References Cited

U.S. PATENT DOCUMENTS

| | | | |
|---|---|---|---|
| 6,755,784 | B2 | 6/2004 | Williams et al. |
| 6,952,681 | B2 | 10/2005 | McQuade et al. |
| 7,058,584 | B2 | 6/2006 | Kosinski et al. |
| 7,668,730 | B2 | 2/2010 | Reardan et al. |
| 7,765,106 | B2 | 7/2010 | Reardan et al. |
| 7,765,107 | B2 | 7/2010 | Reardan et al. |
| 7,797,171 | B2 | 9/2010 | Reardan et al. |
| 7,895,059 | B2 | 2/2011 | Reardan et al. |
| 8,457,988 | B1 | 6/2013 | Reardan et al. |
| 8,589,182 | B1 | 11/2013 | Reardan et al. |
| 2001/0001144 | A1 | 5/2001 | Kapp |
| 2001/0042050 | A1 | 11/2001 | Fletcher et al. |
| 2001/0047281 | A1 | 11/2001 | Keresman, III et al. |
| 2002/0010661 | A1 | 1/2002 | Waddington et al. |
| 2002/0032581 | A1 | 3/2002 | Reitberg |
| 2002/0032582 | A1 | 3/2002 | Feeney, Jr. et al. |
| 2002/0042725 | A1 | 4/2002 | Mayaud |
| 2002/0042762 | A1 | 4/2002 | McQuade et al. |
| 2002/0052762 | A1 | 5/2002 | Kobylevsky et al. |
| 2002/0161607 | A1 | 10/2002 | Subich |
| 2002/0177232 | A1 | 11/2002 | Melker et al. |
| 2003/0033168 | A1 | 2/2003 | Califano et al. |
| 2003/0046110 | A1 | 3/2003 | Gogolak |
| 2003/0050731 | A1* | 3/2003 | Rosenblum ............ 700/232 |
| 2003/0050802 | A1 | 3/2003 | Jay et al. |
| 2003/0074225 | A1 | 4/2003 | Borsand et al. |
| 2003/0093295 | A1 | 5/2003 | Lilly et al. |
| 2003/0110060 | A1 | 6/2003 | Clementi |
| 2003/0127508 | A1 | 7/2003 | Jones |
| 2003/0144876 | A1 | 7/2003 | Kosinski et al. |
| 2003/0160698 | A1 | 8/2003 | Andreasson et al. |
| 2003/0197366 | A1 | 10/2003 | Kusterbeck |
| 2003/0229519 | A1 | 12/2003 | Eidex et al. |
| 2003/0233256 | A1 | 12/2003 | Cardenas et al. |
| 2004/0008123 | A1 | 1/2004 | Carrender et al. |
| 2004/0019567 | A1 | 1/2004 | Herceg et al. |
| 2004/0019794 | A1 | 1/2004 | Moradi et al. |
| 2004/0078237 | A1 | 4/2004 | Kaafarani et al. |
| 2004/0107117 | A1 | 6/2004 | Denny |
| 2004/0117126 | A1 | 6/2004 | Fetterman et al. |
| 2004/0122712 | A1 | 6/2004 | Hill, Sr. et al. |
| 2004/0122713 | A1 | 6/2004 | Hill, Sr. et al. |
| 2004/0162740 | A1 | 8/2004 | Ericsson et al. |
| 2004/0176985 | A1 | 9/2004 | Lilly et al. |
| 2005/0090425 | A1 | 4/2005 | Reardan et al. |
| 2005/0216309 | A1 | 9/2005 | Reardan et al. |
| 2005/0222874 | A1 | 10/2005 | Reardan et al. |
| 2010/0138237 | A1 | 6/2010 | Reardan et al. |
| 2011/0119085 | A1 | 5/2011 | Reardan et al. |
| 2012/0209623 | A1 | 8/2012 | Reardan et al. |

OTHER PUBLICATIONS

"An Interview with Orphan Medical about Xyrem", http://www.talkaboutsleep.com/sleepdisorders/archives/Narcolepsy_xyrem_interview.htm, (Feb. 12, 2001), 3 pgs.

"U.S. Appl. No. 10/322,348, Advisory Action mailed Feb. 5, 2007", 3 pgs.

"U.S. Appl. No. 10/322,348, Appeal Brief filed May 21, 2007", 32 pgs.

"U.S. Appl. No. 10/322,348, Examiner Interview Summary mailed Oct. 21, 2009", 3 pgs.

"U.S. Appl. No. 10/322,348, Final Office Action mailed Oct. 18, 2006", 14 pgs.

"U.S. Appl. No. 10/322,348, Final Office Action mailed Dec. 29, 2005", 11 pgs.

"U.S. Appl. No. 10/322,348, Non Final Office Action mailed Jun. 17, 2005", 26 pgs.

"U.S. Appl. No. 10/322,348, Non Final Office Action mailed Jun. 19, 2006", 18 pgs.

"U.S. Appl. No. 10/322,348, Non Final Office Action mailed Jun. 29, 2005", 12 pgs.

"U.S. Appl. No. 10/322,348, Notice of Allowance mailed Dec. 31, 2009", 16 pgs.

"U.S. Appl. No. 10/322,348, Preliminary Amendment mailed Sep. 30, 2004", 11 pgs.

"U.S. Appl. No. 10/322,348, Reply Brief filed Dec. 3, 2007", 4 pgs.

"U.S. Appl. No. 10/322,348, Response filed Jan. 17, 2007 to Final Office Action mailed Oct. 18, 2006", 17 pgs.

"U.S. Appl. No. 10/322,348, Response filed Mar. 29, 2006 to Final Office Action mailed Dec. 29, 2005", 11 pgs.

"U.S. Appl. No. 10/322,348, Response filed Aug. 8, 2006 to Non Final Office Action mailed Jun. 19, 2006", 10 pgs.

"U.S. Appl. No. 10/322,348, Response filed Sep. 29, 2005 to Non Final Office Action mailed Jun. 29, 2005", 19 pgs.

"U.S. Appl. No. 10/731,915, Non Final Office Action mailed Sug. 12, 2005", 22 pgs.

"U.S. Appl. No. 10/731,915, Non Final Office Action mailed Oct. 5, 2004", 21 pgs.

"U.S. Appl. No. 10/731,915, Non Final Office Action Response mailed Feb. 2, 2005", 17 pgs.

"U.S. Appl. No. 10/979,665, Non-Final Office Action mailed Nov. 17, 2009", 19 pgs.

"U.S. Appl. No. 10/979,665, Notice of Allowance mailed Apr. 30, 2010", 8 pgs.

"U.S. Appl. No. 10/979,665, Preliminary Amendment filed Jun. 22, 2006", 7 pgs.

"U.S. Appl. No. 10/979,665, Preliminary Amendment mailed Nov. 2, 2004", 3 pgs.

"U.S. Appl. No. 10/979,665, Response filed Mar. 11, 2010 to Non Final Office Action mailed Nov. 17, 2009", 13 pgs.

"U.S. Appl. No. 10/979,665, Response filed Jul. 14, 2009 to Restriction Requirement mailed Jun. 25, 2009", 8 pgs.

"U.S. Appl. No. 10/979,665, Restriction Requirement mailed Jun. 25, 2009", 7 pgs.

"U.S. Appl. No. 11/097,651, Examiner Interview Summary mailed May 27, 2010", 3 pgs.

"U.S. Appl. No. 11/097,651, Final Office Action mailed Nov. 12, 2009", 14 pgs.

"U.S. Appl. No. 11/097,651, Non-Final Office Action mailed Mar. 3, 2010", 19 pgs.

"U.S. Appl. No. 11/097,651, Non-Final Office Action mailed May 27, 2009", 21 pgs.

"U.S. Appl. No. 11/097,651, Notice of Allowance mailed Jul. 23, 2010", 9 pgs.

"U.S. Appl. No. 11/097,651, Preliminary Amendment mailed Apr. 1, 2005", 6 pgs.

"U.S. Appl. No. 11/097,651, Response filed Feb. 9, 2010 to Final Office Action mailed Nov. 12, 2009", 11 pgs.

"U.S. Appl. No. 11/097,651, Response filed Jun. 3, 2010 to Non Final Office Action mailed Mar. 3, 2010", 12 pgs.

"U.S. Appl. No. 11/097,651, Response filed Sep. 17, 2009 to Non Final Office Action mailed May 29, 2009", 10 pgs.

"U.S. Appl. No. 11/097,985, Non Final Office Action mailed Sep. 14, 2009", 22 pgs.

"U.S. Appl. No. 11/097,985, Notice of Allowance mailed Mar. 10, 2010", 11 pgs.

"U.S. Appl. No. 11/097,985, Preliminary Amendment mailed Apr. 1, 2005", 7 pgs.

"U.S. Appl. No. 11/097,985, Response filed Nov. 3, 2009 to Non Final Office Action mailed Sep. 14, 2009", 15 pgs.

"U.S. Appl. No. 11/097,985, Supplemental Notice of Allowability mailed Jun. 29, 2010", 3 pgs.

"U.S. Appl. No. 12/704,097, Non-Final Office Action mailed Sep. 24, 2010", 5 pgs.

"U.S. Appl. No. 12/704,097, Notice of Allowance mailed Dec. 21, 2010", 8 pgs.

"U.S. Appl. No. 12/704,097, Response filed Nov. 4, 2010 to Non Final Office Action mailed Sep. 24, 2010", 12 pgs.

"U.S. Appl. No. 13/013,680, Response filed Jun. 12, 2012 to Restriction Requirement mailed Dec. 14, 2011", 9 pgs.

"U.S. Appl. No. 13/013,680, Restriction Requirement mailed Dec. 14, 2011", 7 pgs.

"U.S. Appl. No. 13/013,680, Preliminary Amendment filed Jun. 13, 2012", 4 pgs.

(56) References Cited

OTHER PUBLICATIONS

"Civil Docket", *Jazz Pharmaceuticals, Inc.* v. *Roxane Laboratories, Inc.*, (United States District Court, District of New Jersey Civil Action No. 2:10-CV-06108-ES-CLW), (Nov. 22, 2010), 15 pgs.

"Complaint for Patent Infringement", *Jazz Pharmaceuticals, Inc.* v. *Roxane Laboratories, Inc.*, (United States District Court, District of New Jersey Civil Action No. 10-6108 (ES) (CLW)), (Nov. 22, 2010), 14 pgs.

"Diversion Prevention Through Responsible Distribution", NADDI Regional Training, (May 2001), 12 pages.

"Diversion Prevention Through Responsible Distribution", NADDI Regional Training Tennessee, (Jun. 2001), 14 Pages.

"Diversion Prevention Through Responsible Distribution", NADDI National Conference, (Nov. 2001), 15 pages.

"Jazz Pharmaceuticals, Inc.'s Opening Markman Brief", *Jazz Pharmaceuticals, Inc.* v. *Roxane Laboratories, Inc.*, United States District Court, District of New Jersey Civil Action No. 10-6108 (ES) (CLW), (Dec. 5, 2011), 34 pgs.

"Jazz Pharmaceuticals, Inc.'s Responsive Markman Brief", *Jazz Pharmaceuticals, Inc.* v. *Roxane Laboratories, Inc.*, (United States District Court, District of New Jersey Civil Action No. 10-6108 (ES) (CLW)), (Feb. 21, 2012), 41 pgs.

"Joint Claim Construction and Prehearing Statement", *Jazz Pharmaceuticals, Inc.* v. *Roxane Laboratories, Inc.*, (United States District Court, District of New Jersey Civil Action No. 10-6108 (ES) (CLW)), (Oct. 21, 2011), 31 pgs.

"Letter dated Oct. 14, 2010 from Randall S. Wilson (Roxane Labs) to Bruce C. Cozadd (Jazz Pharmaceuticals)", Re: Patent Notice Pursuant to Section 505(b)(3)(B) [21 USC Sec. 355(b)(3)(B)], (Oct. 14, 2010), 11 pgs.

"Letter from Theodora McCormick to Magistrate Judge Cathy L. Weldor", (w/ Exhibits), (Feb. 27, 2012), 60 pgs.

"Letter from Theodora McCormick to Magistrate Judge Cathy L. Weldor", (w/ Exhibits), (Mar. 19, 2012), 104 pgs.

"Letter from Theodora McCormick to Magistrate Judge Cathy L. Weldor", (Mar. 29, 2012), 4 pgs.

"NASCSA National Conference", Orphan Medical, Inc., (Nov. 2000), 8 pgs.

"Peripheral and Central Nervous System Drugs Advisory Committee", Department of Health and Human Services Food and Drug Administration Center for Drug Evaluation and Research, Holiday Inn, Bethesda, Maryland, (Jun. 6, 2001), 7 pages.

"Preliminary Amendment pursuant to 37 CFR Sec. 1.115", U.S. Appl. No. 11/104,013, filed Apr. 12, 2005, 3 pgs.

"Reply to Counterclaims", *Jazz Pharmaceuticals, Inc.* v. *Roxane Laboratories, Inc.*, (United States District Court, District of New Jersey Civil Action No. 10-6108 (SDW) (MCA), (Feb. 7, 2011), 37 pgs.

"Reply to Counterclaims", *Jazz Pharmaceuticals, Inc.* v. *Roxane Laboratories, Inc.*, (United States District Court, District of New Jersey Civil Action No. 11-660 (SDW) (MCA) Lead Action CV-10-6108), (Apr. 18, 2011), 6 pgs.

"Roxane Laboratories, Inc.'s Answer, Affirmative Defenses and Counterclaims to Plaintiff's Complaint", *Jazz Pharmaceuticals, Inc.* v. *Roxane Laboratories, Inc.*, (United States District Court, District of New Jersey Civil Action No. 10-6108 (ES) (CLW), (Dec. 29, 2010), 21 pgs.

"Roxane Laboratories, Inc.'s Initial Invalidity and Noninfringement Contentions Pursuant to Local Patent Rule 3.6", *Jazz Pharmaceuticals, Inc.* v. *Roxane Laboratories, Inc.*, (United States District Court, District of New Jersey Civil Action No. 2:10-cv-06108 (SDW) (MCA)), (Apr. 14, 2011), 317 pgs.

"Roxane Laboratories, Inc.'s Opening Markman Brief in Support of Its Claim Constructions", *Jazz Pharmaceuticals, Inc.* v. *Roxane Laboratories, Inc.*, (United States District Court, District of New Jersey Civil Action No. 2.10-cv-06108 (ES) (CLW)), (Dec. 5, 2011), 37 pgs.

"Roxane Laboratories, Inc.'s Responsive Markman Brief in Support of Its Claim Constructions", *Jazz Pharmaceuticals, Inc.* v. *Roxane Laboratories, Inc.*, (United States District Court, District of New Jersey Civil Action No. 2:10-cv-06108 (ES) (CLW)), (Feb. 21, 2012), 27 pgs.

"System for Thalidomide Education and Prescribing Safety (S.T.E.P.S.) Starter Kit", Celgene Corporation, (2001), 103 pgs.

Ukens, C., "Specialty Pharmacy", Drug Topics, 144, (Jun. 5, 2000), 40-47.

"U.S. Appl. No. 13/595,757, Non Final Office Action mailed Jan. 17, 2013", 6 pgs.

"Markman Opinion, filed Sep. 14, 2012, in the case of *Jazz Pharmaceuticals, Inc.*, Plaintiff, v. *Roxane Laboratories, Inc.*, Defendant (United States District Court for the District of New Jersey, Civil 10-6108 ES)", 43 pgs.

"Roxane Laboratories, Inc.'s Answer and Affirmative Defenses to Plaintiff's Complaint", (Jan. 4, 2013), 8 pgs.

"Roxane Laboratories, Inc.'s Answer, Affirmative Defenses and Counterclaims to Plaintiff's Complaint", (Mar. 9, 2011), 13 pgs.

"Roxane Laboratories, Inc.'s Answer, Affirmative Defenses and Counterclaims to Plaintiff's Complaint", (Jun. 1, 2011), 12 pgs.

"Roxane Laboratories, Inc.'s Answer, Affirmative Defenses and Counterclaims to Plaintiff's Complaint", (Nov. 9, 2012), 18 pgs.

"Briefing Booklet for the Peripheral and Central Nervous System Drugs Advisory Committee Meeting", Orphan Medical, Inc., (Jun. 6, 2001), 353 pgs.

"Civil Cover Sheet", *Jazz Pharmaceuticals, Inc.* v. *Amneal Pharmaceuticals, LLC*, (United States District Court, District of New Jersey, (Jan. 18, 2013), 2 pgs.

"Complaint for Patent Infringement", *Jazz Pharmaceuticals, Inc.* v. *Amneal Pharmaceuticals, LLC*, (United States District Court, District of New Jersey, (Jan. 18, 2013), 17 pgs.

"Controlled Substances Act", Drugs of Abuse, U.S. Department of Justice, Drug Enforcement Administration, (1997), 9 pgs.

"Detailed Factual and Legal Basis of Non-Infringement and/or Invalidity", Amneal Pharmaceuticals, LLC, (Dec. 12, 2012), 3 pgs.

"Detailed Factual and Legal Basis of Non-Infringement and/or Invalidity", Amneal Pharmaceuticals, LLC, (Dec. 7, 2012), 6 pgs.

"Exhibits A-D", *Jazz Pharmaceuticals* v *Amneal Pharmaceuticals, LLC*, (Jan. 18, 2013), 151 pgs.

"Exhibits D-G", *Jazz Pharmaceuticals* v *Amneal Pharmaceuticals, LLC*, (Jan. 18, 2013), 123 pgs.

"Fed. R. Civ. P. Rule 7.1 Disclosure Statement", (Jan. 18, 2013), 2 pgs.

"Making Good in Your Own Mail-Order Business", Changing Times—The Kiplinger Magazine, (Oct. 1980), 66-68.

"Notice of Electronic Filing: Civil Inital Pleadings (Attorney/Credit Card) Use Case 33-1", US District Court, District of new Jersey [LIVE], (Jan. 18, 2013), 2 pgs.

"Notice of Paragraph IV Certification Concerning ANDA 203631 for Sodiium Oxybate Oral Solution, 500 mg/mL", Amneal Pharmaceuticals, LLC, (Dec. 7, 2012), 4 pgs.

"Notice of Paragraph IV Certification Concerning ANDA 203631 for Sodiium Oxybate Oral Solution. 500 mg/mL", Amneal Pharmaceuticals, LLC, (Dec. 12, 2012), 4 pgs.

"Peripheral and Central Nervous System Drugs Advisory Committee—Transcript", Department of Health and Human Services Food and Drug Administration Center for Drug Evaluation and Research, Holiday Inn, Bethesda, Maryland, (Jun. 6, 2001), 381 pgs.

"Xyrem Prescription and Distribution Process-Video Script", (Feb. 2, 2001), 10 pgs.

Deutsch, Sheryl, "The Verification and Information-Gathering Process", The Credentialing Handbook, Aspen Publishers, Inc., (1999), 231-275.

Mani, Ranjit, "Preliminary Clinical Safety Review of NDA No. 21196", Orphan Medical, Inc., (May 3, 2001), 122 pgs.

"U.S. Appl. No. 13/595,676, Notice of Allowance mailed Sep. 17, 2013", 8 pgs.

"Civil Cover Sheet", *Jazz Pharmaceuticals, Inc.* v. *Amneal Pharmaceuticals, LLC*, (United States District Court, District of New Jersey), (Sep. 12, 2013), 2 pgs.

"Complaint for Patent Infringement with Exhibit A", *Jazz Pharmaceuticals, Inc.* v. *Amneal Pharmaceuticals, LLC*, (United States District Court, District of New Jersey), (Sep. 12, 2013), 76 pgs.

(56) References Cited

OTHER PUBLICATIONS

"Fed. R. Civ. P. Rule 7.1 Disclosure Statement", *Jazz Pharmaceuticals, Inc.* v. *Amneal Pharmaceuticals, LLC,* (United States District Court, District of New Jersey), (Sep. 12, 2013), 2 pgs.

"Notice of Electronic Filing: Civil Initial Pleadings (Attorney/Credit Card) Use Case 33-1)", *Jazz Pharmaceuticals, Inc.* v. *Amneal Pharmaceuticals, LLC,* (United States District Court, District of New Jersey [LIVE]), (Sep. 12, 2013), 1 pg.

"U.S. Appl. No. 13/595,676, Response filed May 31, 2013 to Non Final Office Action mailed Mar. 21, 2013", 14 pgs.

"U.S. Appl. No. 13/595,676, Examiner Interview Summary mailed May 30, 2013", 3 pgs.

"Notice of Paragraph IV Certification", Detailed Statement of the Factual and Legal Bases for Pars Paragraph IV Patent Certification and Offer of Confidential Access, (Nov. 20, 2013), 190 pgs.

Oxtoby, David W, et al., "", Principles of Modern Chemistry, Fort Worth : Saunders College Pub., (1996), 52-56.

"Civil Action No. 2:13-cv-00391-ES-SCM (consolidated)", Defendant Amneal Pharmaceuticals, LLC's Preliminary Invalidity Contentions (United States District Court of New Jersey), 182 pgs.

"Civil Cover Sheet", *Jazz Pharmaceuticals, Inc.* v. *Par Pharmaceuticals, Inc.*, (United States District Court, District of New Jersey), (Dec. 27, 2013), 1 pg.

"Complaint for Patent Infringement", *Jazz Pharmaceuticals, Inc.* v. *Par Pharmaceuticals, Inc*, (United States District Court, District of New Jersey), (Dec. 27, 2013), 26 pgs.

"Fed. R. Civ. P. Rule 7.1 Disclosure Statement", *Jazz Pharmaceuticals, Inc.* v. *Par Pharmaceuticals, Inc.*, (United States District Court, District of New Jersey), (Dec. 27, 2013), 2 pgs.

"Final Minutes: Peripheral and Central Nervous System Drugs Advisory Committee", [Online]. Retrieved from the Internet: <URL: http://www.fda.gov/ohrms/dockets/ac/01/minutes/3754m1.htm>, (Jun. 6, 2001), 6 pgs.

"Notice of Paragraph IV Certification", Detailed Statement of the Factual and Legal Bases for Pars Paragraph IV Patent Certification and Offer of Confidential Access, (Dec. 20, 2013), 190 pgs.

"Orphan Medical Slides: Xyrem (sodium oxybate) oral solution", Peripheral and Central Nervous System Drugs Advisory Committee Meeting, [Online]. Retrieved from the Internet: <URL: http://www.fda.gov/ohrms/dockets/ac/01/slides/3754s1_01_orphanmedical/index.htm>, (Jun. 6, 2001), 167 pgs.

"Report on the Filing or Determination of an Action Regarding a Patent or Trademark", *Jazz Pharmaceuticals, Inc.* v. *Par Pharmaceuticals, Inc.*, United States District Court, District of New Jersey Case No. 2:13-cv-07884-ES-JAD, (Dec. 27, 2013), 1 pg.

"Slides: Pediatric Subcommittee of the Peripheral and Central Nervous system Drugs Advisory Committee", [Online]. Retrieved from the Internet: <URL: http://www.fda.gov/ohrms/dockets/ac/01/slides/3754s1.htm>, (Jun. 6, 2001), 86 pgs.

"Summons in a Civil Case", *Jazz Pharmaceuticals, Inc.* v. *Par Pharmaceuticals, Inc.*, United States District Court, District of New Jersey Case No. 213-CV-07884-ES-JAD, (Dec. 31, 2013), 2 pgs.

Oxtoby, David W, et al., Principles of Modern Chemistry, Fort Worth: Saunders College Pub., (1996), 52-56.

U.S. Appl. No. 13/595,676, Non Final Office Action mailed Mar. 21, 2013, 16 pgs.

U.S. Appl. No. 13/595,757, Examiner Interview Summary mailed Mar. 12, 2013, 3 pgs.

U.S. Appl. No. 13/595,757, Notice of Allowance mailed Mar. 21, 2013, 68 pgs.

U.S. Appl. No. 13/595,757, Response filed Mar. 7, 2013 to Non Final Office Action mailed Jan. 17, 2013, 8 pgs.

"Roxane Laboratories, Inc.'s Amended Answer and Affirmative Defenses to Plaintiffs Complaint Regarding U.S. Patent No. 8,234,275", Exhibit 2, (Apr. 26, 2013), 15 pgs.

"Roxane Laboratories, Inc.'s Amended Answer, Affirmative Defenses and Counterclaims to Plaintiffs Complaint Regarding U.S. Patent No. 8,263,650", Exhibit 1, (Apr. 26, 2013), 23 pgs.

"Answer, Defenses, and Counterclaims", *Jazz Pharmaceuticals, Inc.* v. *Amneal Pharmaceuticals, LLC,* (United States District Court, District of New Jersey Civil Action No. 13-391 ES-SCM, (Apr. 15, 2013), 22 pgs.

"Notice of Voluntary Dismissal of Counterclaims Pertaining to U.S. Patent Nos. 7,668,730; 7,765,106; and 7,765,107 (Contained in Counts I, II) Pursuant to Fed. R. Civ. P. 41(a), (c)", *Jazz Pharmaceuticals, Inc.* v. *Amneal Pharmaceuticals, LLC*, (United States District Court, District of New Jersey Civil Action No. 13-391 ES-SCM, (Jul. 15, 2013), 2 pgs.

\* cited by examiner

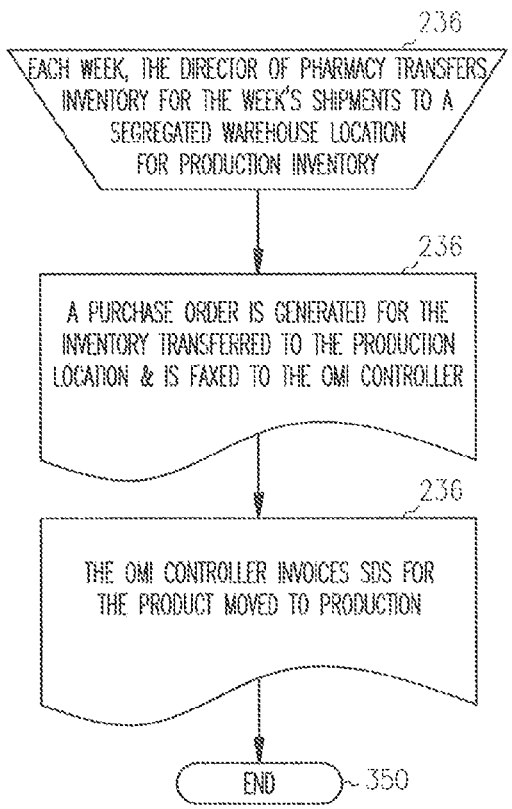
FIG. 6
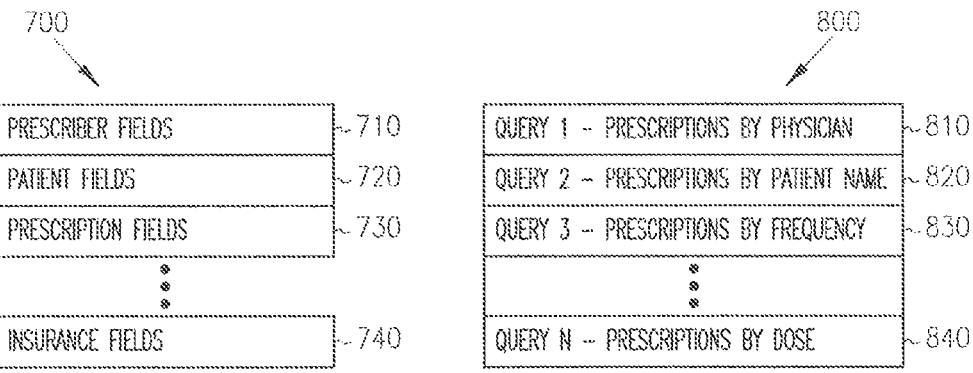
FIG. 7
FIG. 8

PRESCRIPTION AND ENROLLMENT FORM

PRESCRIBER INFORMATION

PRESCRIBER'S NAME: _____ OFFICE CONTACT: _____
STREET ADDRESS: _____
CITY: _____ STATE: _____ ZIP: _____
PHONE: _____ FAX: _____
LICENSE NUMBER: _____ DEA NUMBER: _____
MD SPECIALTY: _____

PRESCRIPTION FORM

PATIENT NAME: _____ SS#: _____ DOB: _____ SEX M / F
ADDRESS: _____
CITY: _____ STATE: _____ ZIP: _____
Rx: XYREM ORAL SOLUTION (500 mg/mL) 180 ML BOTTLE QUANTITY: _____ MONTHS SUPPLY
SIG: TAKE _____ GMS P.O. DILUTED IN 60 mL WATER AT H.S. AND THEN AGAIN 2 1/2 TO 4 HOURS LATER
REFILLS (CIRCLE ONE): 0 1 2 (MAXIMUM OF 3 MONTH SUPPLY)
_____ DATE: ___/___/___
PRESCRIBER'S SIGNATURE

| PHYSICIAN DECLARATION—PLEASE CHECK EACH BOX | TO BE COMPLETED AT INITIAL PRESCRIPTION ONLY |
|---|---|

☐ I HAVE READ THE MATERIALS IN THE XYREM PHYSICIAN SUCCESS PROGRAM
☐ I VERIFY THAT THE PATIENT HAS BEEN EDUCATED WITH RESPECT TO XYREM PREPARATION, DOSING AND SCHEDULING.
☐ I UNDERSTAND THAT XYREM IS APPROVED FOR THE TREATMENT OF CATAPLEXY IN PATIENTS WITH NARCOLEPSY, AND THAT SAFETY OR EFFICACY HAS NOT BEEN ESTABLISHED FOR ANY OTHER INDICATION.
☐ I UNDERSTAND THAT THE SAFETY OF DOSES GREATER THAN 9gm/DAY HAS NOT BEEN ESTABLISHED

PATIENT INFORMATION

BEST TIME TO CONTACT PATIENT: ☐ DAY ☐ NIGHT
DAY #: _____ EVENING #: _____
INSURANCE COMPANY NAME: _____ PHONE #: _____
INSURED'S NAME: _____ RELATIONSHIP TO PATIENT: _____
IDENTIFICATION NUMBER: _____ POLICY/GROUP NUMBER: _____
PRESCRIPTION CARD: ☐ NO ☐ YES IF YES, CARRIER: _____ POLICY #: _____ GROUP: _____
PLEASE ATTACH COPIES OF PATIENT'S INSURANCE CARDS

FAX COMPLETED FORM TO XYREM SUCCESS PROGRAM (TOLL-FREE) 1-866-470-1744
FOR INFORMATION, CALL THE XYREM TEAM (TOLL FREE) AT 1-866-XYREM88 (1-866-997-3688)

FIG. 9

PATIENT ASSISTANCE APPLICATION REQUEST FORM

DATE:

TO: PATIENT ASSISTANCE ORGANIZATION
FROM: SDS

FAX #: 203-798-2291

PLEASE SEND A XYREM PATIENT ASSISTANCE PROGRAM APPLICATION TO:

PATIENT NAME _____
ADDRESS _____
_____

TELEPHONE: (   ) _____

PATIENT DOSAGE: _____ (GRAMS) TWICE NIGHTLY FOR A TOTAL DOSAGE OF _____ (GRAMS)
_____ BOTTLES (THREE MONTHS SUPPLY)
BACKGROUND INFORMATION:
_____
_____
_____
_____
_____
_____

SENSITIVE DRUG PATIENT ASSISTANCE PROGRAM  1100
VOUCHER REQUEST FOR MEDICATION

PATIENT INFORMATION
<FIRST NAME><LAST NAME>
<ADDRESS 1>
<ADDRESS 2>
<CITY, STATE ZIP CODE>

PHONE: <123-456-7890
DOB: 01/01/1900
SSN: 123-45-6789          CASE CODE: ********
DRUG ALLOTMENT: 100%
LRD: 03/01/2001

PHYSICIAN INFORMATION
<PHYSICIAN NAME>
<ADDRESS 1>
<ADDRESS 2>
<CITY, STATE ZIP CODE>

PHONE: <123-456-7890

FIRST SHIPMENT THIS YEAR

| DRUG | QUANTITY |
|---|---|
| XYREM 180ml btl | 1 |

| VALIDATION DATE: | 03/01/2001 |
|---|---|
| EXPIRATION DATE: | 05/31/2001 |
| ISSUE DATE: | 03/15/2001 |
| APPROVED _____ | |

*PHARMACY USE*

NORD COPY
*************************************************************
(DETACH HERE)

PATIENT INFORMATION
<FIRST NAME><LAST NAME>
<ADDRESS 1>
<ADDRESS 2>
<CITY, STATE ZIP CODE>

PHONE: <123-456-7890
DOB: 01/01/1900
SSN: 123-45-6789          CASE CODE: ********
DRUG ALLOTMENT: 100%
LRD: 03/01/2001

PHYSICIAN INFORMATION
<PHYSICIAN NAME>
<ADDRESS 1>
<ADDRESS 2>
<CITY, STATE ZIP CODE>

PHONE: <123-456-7890

FIRST SHIPMENT THIS YEAR

| DRUG | QUANTITY |
|---|---|
| XYREM 180ml btl | 1 |

| VALIDATION DATE: | 03/01/2001 |
|---|---|
| EXPIRATION DATE: | 05/31/2001 |
| ISSUE DATE: | 03/15/2001 |
| APPROVED _____ | |

*PHARMACY USE*

FIG. 11

SENSITIVE DRUG PHYSICIAN'S CERTIFICATE
OF MEDICAL NEED

PATIENT INFORMATION

DATE: ...............

NAME: ..................................................................................................
    LAST                FIRST                        M

DATE OF BIRTH: ....................................

DRUG BEING PRESCRIBED: XYREM

DIAGNOSIS/CONDITION FOR WHICH DRUG IS BEING PRESCRIBED: ..................

ICD-9: ...............

PHYSICIAN INFORMATION

PHYSICIAN'S NAME (PLEASE PRINT): ..........................................

PHYSICIAN'S SIGNATURE: ...................................... DATE: ................

PLEASE FAX BACK TO SENSITIVE DRUG SUCCESS PROGRAM: (1-800-TOLL FREE NUMBER)

FIG. 12

ACTIVITY REPORTS

| | REPORT FREQUENCY | | |
|---|---|---|---|
| | WEEKLY | MONTHLY | QUARTERLY |
| SALES | | | |
| Rx BY ZIP (NEW AND TOTAL) | X | X | X |
| Rx BY PHYSICIAN BY ZIP | X | X | |
| $ BY ZIP | X | X | X |
| REGULATORY | | | |
| # OF PHYSICIAN REGISTRIES | | X | |
| # OF DENIED PHYSICIAN REGISTRIES AND REASON | | X | |
| # OF COMPLETED PATIENT REGISTRIES | | X | |
| # OF PROBLEM IDENTIFICATION & MANAGEMENT RISK DIVERSION REPORTS COMPLETED | X | | |
| # OF CYCLE COUNTS PERFORMED & ACCURACY OF EACH | | X | |
| QUALITY ASSURANCE | | | |
| # OF PRODUCT DEFECTS/COMPLAINTS REPORTED, TYPE AND LOT # | | X | |
| CALL CENTER | | | |
| # OF CALLS RECEIVED | | X | |
| # OF CALLS INITIATED | | X | |
| # OF CALLS ANSWERED IN 30 SECONDS, ETC. | | X | |
| PERCENTAGE OF CALLS ANSWERED IN 30 SECONDS | | X | |
| # OF ABANDONED CALLS | | X | |
| % OF ABANDONED CALLS | | X | |
| AVERAGE CALL LENGTH | | X | |
| PHARMACY | | | |
| # OF FAXED Rx/ENROLLMENT FORMS | | X | |
| # OF MAILED Rx/ENROLLMENT FORMS | | X | |
| # OF Rx'S SHIPPED WITHIN 1, 2, 3, 4 ETC. DAYS FROM THE TIME INITIAL RECEIPT TO SHIPMENT OF Rx) | | X | |
| # OF PATIENT SUCCESS PACKETS SHIPPED | | X | |

FIG. 13A

ACTIVITY REPORTS

| | | | |
|---|---|---|---|
| PHARMACY | | | |
| # OF PHYSICIAN SUCCESS PACKETS SHIPPED | | | X |
| # OF COMPLETED SHIPMENTS | | | X |
| # OF INCOMPLETE SHIPMENTS AND REASON | | | X |
| # OF SHIPPING ERRORS | | | X |
| # OF PAP SHIPMENTS | | | X |
| # OF PAP APPLICATIONS | | | X |
| # OF PAP APPROVALS | | | X |
| # OF CANCELED ORDERS | | | X |
| # OF USPS ERRORS | | | X |
| INVENTORY | | | |
| # OF RETURNED PRODUCTS AND REASON | | | X |
| # OF OUTDATED BOTTLES OF PRODUCT | | | X |
| INVENTORY COUNTS OF CONSIGNMENT & PRODUCTION INVENTORY | | | X |
| # OF UNITS RECEIVED | | | X |
| LOTS RECEIVED | | | X |
| REIMBURSEMENT | | | |
| # OF PENDED AND WHY | | | X |
| # OF APPROVALS | | | X |
| # OF DENIALS | | | X |
| # OF REJECTIONS | | | X |
| PAYOR TYPES | | | X |

FIG. 13B

ACTIVITY REPORTS

| PATIENT CARE | | |
|---|---|---|
| # OF ADVERSE EVENTS REPORTED AND TYPE | | X |
| # OF ADVERSE EVENTS SENT TO OMI | | X |
| # OF DOSING PROBLEMS AND TYPE | | X |
| # OF NONCOMPLIANCE EPISODES AND REASON | | X |
| # OF PATIENT COUNSELED AND REASON | | X |
| # OF PATIENTS DISCONTINUED AND REASON | | X |
| PATIENT CARE | | |
| # OF PATIENTS REFERRED TO PHYSICIAN AND REASON | | X |
| # OF ACTIVE PATIENTS | | X |
| # OF NEW PATIENTS | | X |
| # OF RESTART PATIENTS | | X |
| # OF DISCONTINUED PATIENTS AND REASON | | X |
| DRUG INFORMATION | | |
| # OF DRUG INFORMATION REQUESTS AND TYPE | | X |
| # OF CALLS TRIAGED TO OMI | | X |

FIG. 13C

SENSITIVE DRUG DISTRIBUTION SYSTEM AND METHOD

RELATED APPLICATION

This application a Continuation of U.S. application Ser. No. 13/013,680, filed on Jan. 25, 2011, which is a Continuation of U.S. application Ser. No. 12/704,097, filed on Feb. 11, 2010 and issued on Feb. 22, 2011 as U.S. Pat. No. 7,895,059, which is a Continuation of U.S. application Ser. No. 10/322, 348, filed on Dec. 17, 2002 and issued on Feb. 23, 2010 as U.S. Pat. No. 7,668,730, which applications are incorporated by reference herein in their entirety.

FIELD OF THE INVENTION

The present invention relates to distribution of drugs, and in particular to the distribution of sensitive drugs.

BACKGROUND OF THE INVENTION

Sensitive drugs are controlled to minimize risk and ensure that they are not abused, or cause adverse reactions. Such sensitive drugs are approved for specific uses by the Food and Drug Administration, and must be prescribed by a licensed physician in order to be purchased by consumers. Some drugs, such as cocaine and other common street drugs are the object of abuse and illegal schemes to distribute for profit. Some schemes include Dr. shopping, diversion, and pharmacy thefts. A locked cabinet or safe is a requirement for distribution of some drugs.

Certain agents, such as gamma hydroxy buterate (GHB) are also abused, yet also are effective for therapeutic purposes such as treatment of daytime cataplexy in patients with narcolepsy. Some patients however, will obtain prescriptions from multiple doctors, and have them filled at different pharmacies. Still further, an unscrupulous physician may actually write multiple prescriptions for a patient, or multiple patients, who use cash to pay for the drugs. These patients will then sell the drug to dealers or others for profit.

There is a need for a distribution system and method that directly addresses these abuses. There is a further need for such a system and method that provides education and limits the potential for such abuse.

SUMMARY OF THE INVENTION

A drug distribution system and method utilizes a central pharmacy and database to track all prescriptions for a sensitive drug. Information is kept in a central database regarding all physicians allowed to prescribe the sensitive drug, and all patients receiving the drug. Abuses are identified by monitoring data in the database for prescription patterns by physicians and prescriptions obtained by patients. Further verification is made that the physician is eligible to prescribe the drug by consulting a separate database for a valid DEA license, and optionally state medical boards to determine whether any corrective or approved disciplinary actions relating to controlled substances have been brought against the physician. Multiple controls beyond those for traditional drugs are imposed on the distribution depending on the sensitivity of the drug.

Education is provided to both physician and patient. Prior to shipping the drug for the first time, the patient is contacted to ensure that product and abuse related educational materials have been received and/or read. The patient may provide the name of a designee to the central pharmacy who is authorized to accept shipment of the drug. Receipt of the initial drug shipment is confirmed by contacting the patient. Either a phone call or other communication to the patient within a set time after delivery may be made to ensure receipt. Further, a courier service's tracking system is used to confirm delivery in further embodiments. If a shipment is lost, an investigation is launched to find it.

In one embodiment, the drug may be shipped by the central pharmacy to another pharmacy for patient pick-up. The second pharmacy's ability to protect against diversion before shipping the drug must be confirmed. This ability may be checked through NTIS and State Boards of Pharmacy.

Prescription refills are permitted in the number specified in the original prescription. In addition, if a prescription refill is requested by the patient prior to the anticipated due date, such refills will be questioned. A lost, stolen, destroyed or spilled prescription/supply is documented and replaced to the extent necessary to honor the prescription, and will also cause a review or full investigation.

The exclusive central database contains all relevant data related to distribution of the drug and process of distributing it, including patient, physician and prescription information. Several queries and reports are run against the database to provide information which might reveal potential abuse of the sensitive drug, such as early refills.

BRIEF DESCRIPTION OF THE DRAWINGS

FIG. 6 is a flowchart of a process for inventory control at least partially utilizing a computer system such as that shown in FIG. 1.

FIG. 7 is a block diagram of database fields.

FIG. 8 is a block diagram showing a list of queries against the database fields.

FIG. 9 is a copy of one example prescription and enrollment form.

FIG. 11 is a copy of one example voucher request for medication for use with the NORD application request form of FIG. 10.

FIG. 12 is a copy of certificate of medical need.

FIGS. 13A, 13B and 13C are descriptions of sample reports obtained by querying a central database having fields represented in FIG. 7.

DETAILED DESCRIPTION OF THE INVENTION

Figure 1:
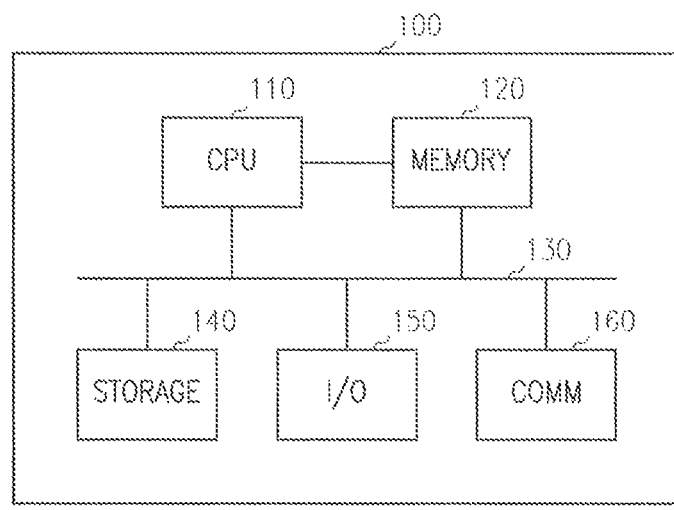
FIG. 1 is a block diagram of a computer system for use in implementing the system and method of the present invention.

In the following description, reference is made to the accompanying drawings that form a part hereof, and in which is shown by way of illustration specific embodiments in which the invention may be practiced. These embodiments are described in sufficient detail to enable those skilled in the art to practice the invention, and it is to be understood that other embodiments may be utilized and that structural, logical and electrical changes may be made without departing from the scope of the present invention. The following description is, therefore, not to be taken in a limited sense, and the scope of the present invention is defined by the appended claims.

The functions or algorithms described herein are implemented in software or a combination of software and human implemented procedures in one embodiment. The software comprises computer executable instructions stored on computer readable media such as memory or other type of storage devices. The term "computer readable media" is also used to represent carrier waves on which the software is transmitted. Further, such functions correspond to modules, which are software, hardware, firmware of any combination thereof. Multiple functions are performed in one or more modules as desired, and the embodiments described are merely examples. The software is executed on a digital signal processor, ASIC, microprocessor, or other type of processor operating on a computer system, such as a personal computer, server or other computer system.

A sensitive drug is one which can be abused, or has addiction properties or other properties that render the drug sensitive. One example of such a drug is sodium oxybate, also known as gamma hydroxy butyrate (GHB $C_4H_7NaO_3$) which is useful for treatment of cataplexy in patients with narcolepsy. GHB is marketed under the trademark of Xyrem® (sodium oxybate oral solution), which trademark can be used interchangeably with GHB herein. Sensitive drugs also include narcotics or other drugs which require controls on their distribution and use to monitor behaviors to prevent abuse and adverse side effects.

In one embodiment, Xyrem® is subject to a restricted distribution program. One aspect of the program is to educate physicians and patients about the risks and benefits of Xyrem, including support via ongoing contact with patients and a toll free helpline. Initial prescriptions are filled only after a prescriber and patient have received and read the educational materials. Further, patient and prescribing physician registries are maintained and monitored to ensure proper distribution.

In a further embodiment, bulk sodium oxybate is manufactured at a single site, as is the finished drug product. Following manufacture of the drug product, it is stored at a facility compliant with FDA Schedule III regulations, where a consignment inventory is maintained. The inventory is owned by a company, and is managed by a central pharmacy, which maintains the consignment inventory. Xyrem® is distributed and dispensed through a primary and exclusive central pharmacy, and is not stocked in retail pharmacy outlets. It is distributed by overnight carriers, or by US mail in one embodiment to potentially invoke mail fraud laws if attempts of abuse occur.

FIG. 1 is a simplified block diagram of a computer system 100, such as a personal computer for implementing at least a portion of the methods described herein. A central processing unit (CPU) 110 executes computer programs stored on a memory 120. Memory 120 in one embodiment comprises one or more levels of cache as desired to speed execution of the program and access to data on which the programs operate. The CPU is directly coupled to memory 120 in one embodiment. Both CPU 110 and memory 120 are coupled to a bus 130. A storage 140, I/O 150 and communications 160 are also coupled to the bus 130. Storage 140 is usually a long term storage device, such as a disk drive, tape drive, DVD, CD or other type of storage device. In one embodiment, storage 140 is used to house a database for use with the present invention. I/O 150 comprises keyboards, sound devices, displays and other mechanisms by which a user interacts with the computer system 100. Communications 160 comprises a network, phone connection, local area network, wide area network or other mechanism for communicating with external devices. Such external devices comprise servers, other peer computers and other devices. In one embodiment, such external device comprises a database server that is used in place of the database on storage 140. Other computer system architectures capable of executing software and interacting with a database and users may also be used. Appropriate security measures such as encryption are used to ensure confidentiality. Further, data integrity and backup measures are also used to prevent data loss.

Figure 2A:
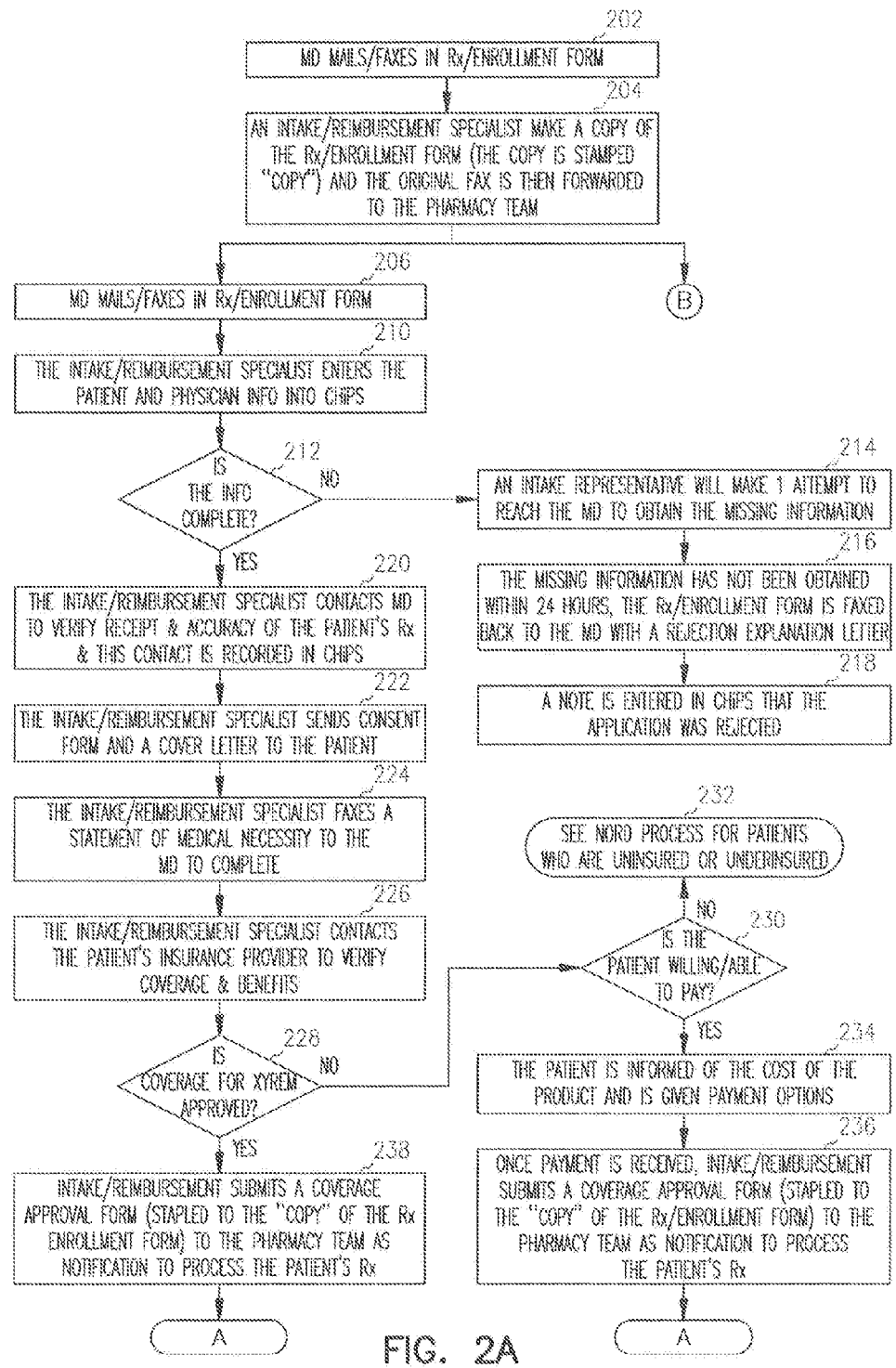
FIGS. 2A, 2B and 2C are a flowchart describing a method for sensitive drug distribution at least partially utilizing a computer system such as that shown in FIG. 1.
Figure 2B:
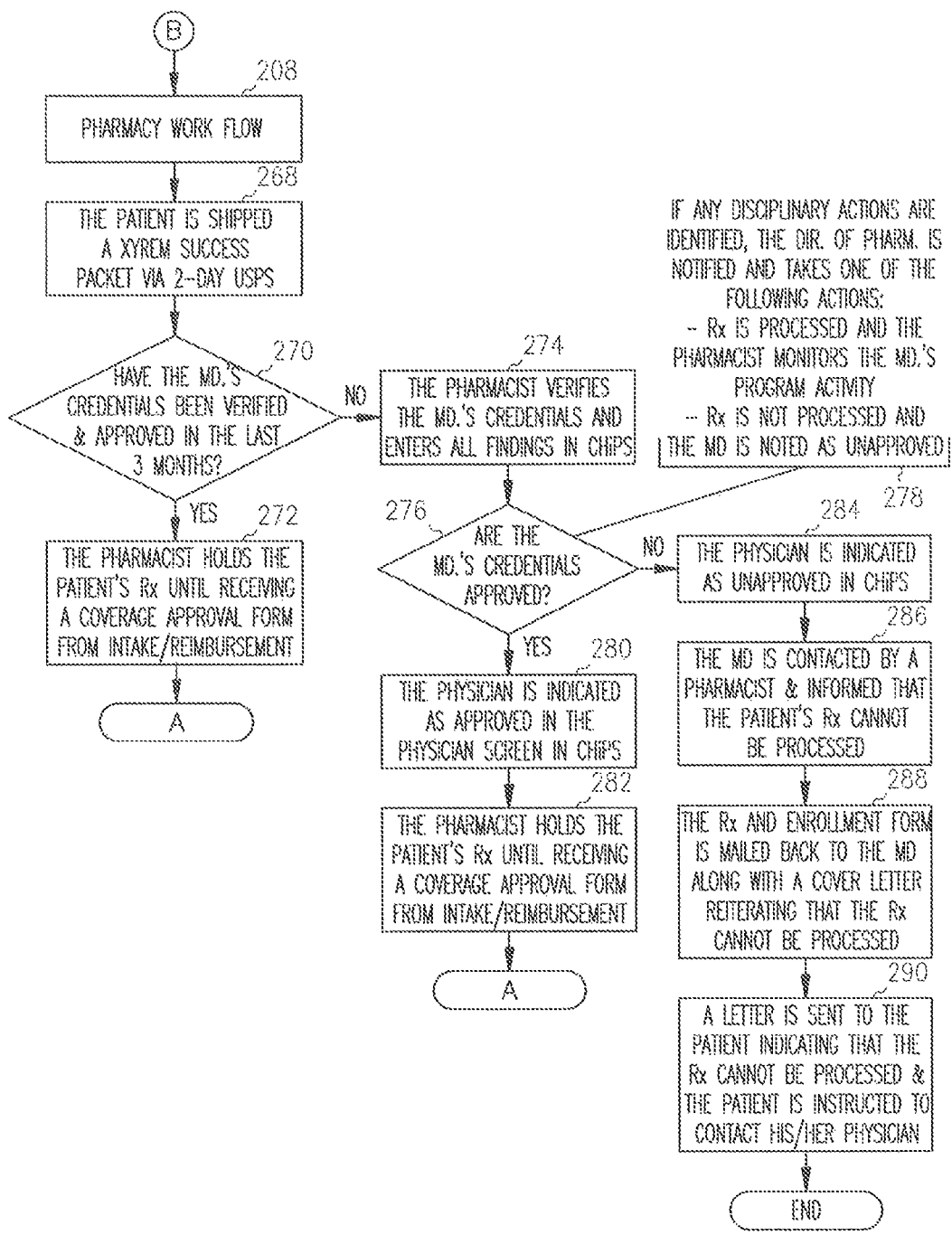
Figure 2C:
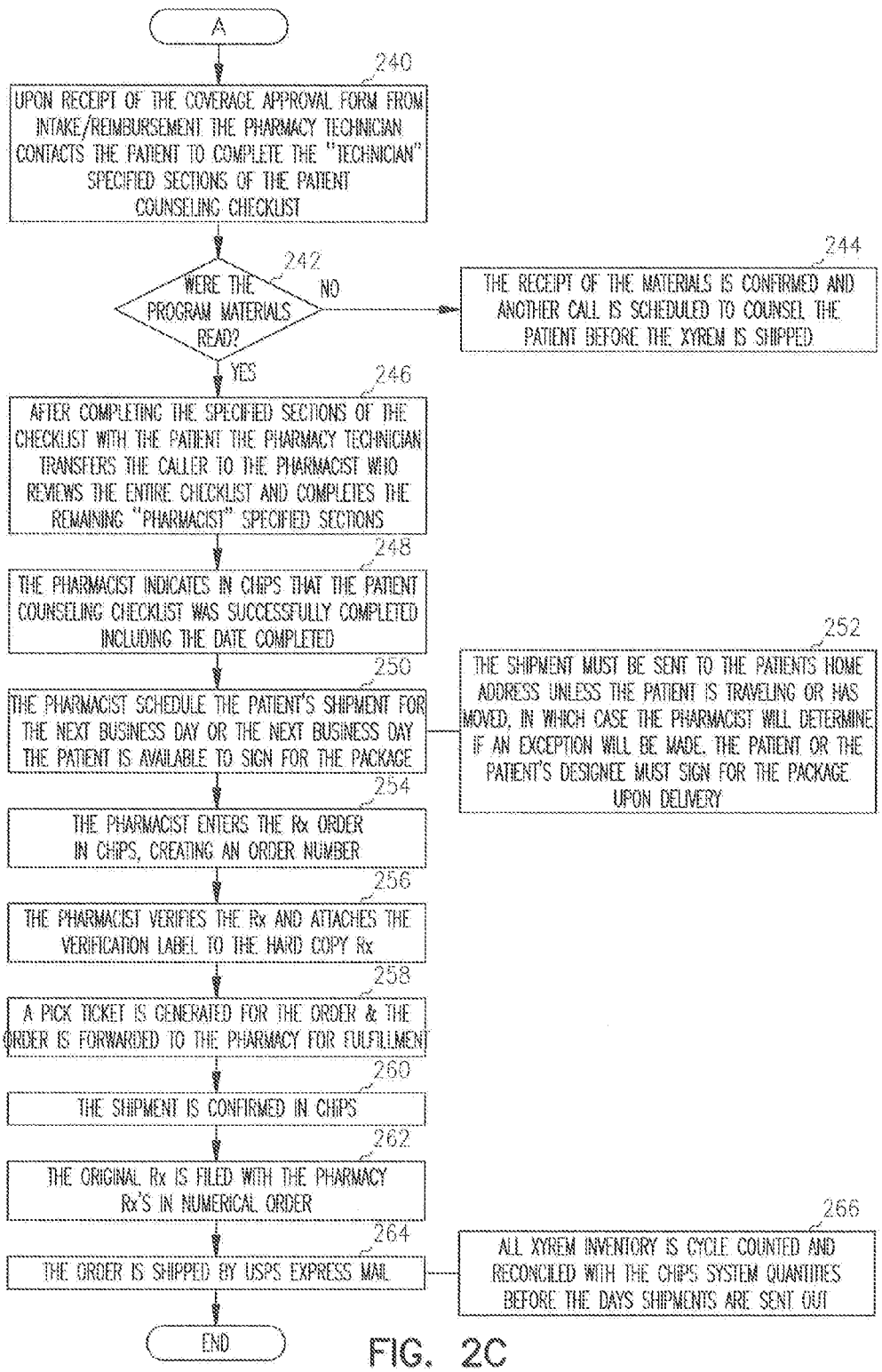

FIGS. 2A, 2B and 2C represent an initial prescription order entry process for a sensitive drug, such as Xyrem. At 202, a medical doctor (MD) sends a Rx/enrollment form via mail, fax, email or other means to an intake/reimbursement specialist at 204, who makes a copy of the RX/enrollment form that is stamped "copy". The original fax is forwarded to a pharmacy team. The enrollment form contains prescriber information, prescription information, checkboxes for the prescriber indicating they have read materials, educated the patient, understand the use in treatment, and understand certain safety information, and also contains patient information.

The prescriber information contains standard contact information as well as license number, DEA number and physician specialty. Patient and prescription information includes name, social security number, date of birth, gender, contact information, drug identification, patient's appropriate dosage, and number of refills allowed, along with a line for the prescriber's signature. Patient insurance information is also provided.

There are two workflows involved at the pharmacy team, intake reimbursement 206 and pharmacy workflow 208, which may proceed in parallel or serially. The intake work flow 206 starts with an intake reimbursement specialist entering the patient and physician information into an application/database referred to as CHIPS, which is used to maintain a record of a client home infusion program (CHIP) for Xyrem®. A check is made to ensure the information is complete at 212. If not, at 214, an intake representative attempts to reach the MD or prescriber to obtain the missing information. If the missing information has not been obtained within a predetermined period of time, such as 24 hours at 216, the Rx/Enrollment form is sent back to the MD with a rejection explanation. A note is entered in CHIPS that the application was rejected.

If the information is complete at 212, the MD is contacted at 220 to verify receipt and accuracy of the patient's Rx. This contact is recorded in CHIPS. The intake and reimbursement specialist then sends a consent form and a cover letter to the patient at 224. The insurance provider is contacted at 226 to verify coverage and benefits. At 228, a determination is made regarding coverage for the drug. If it is not available, it is determined at 230 whether the patient is willing and able to pay. If not, a process is performed for handling patients who are uninsured or underinsured. In one embodiment, the process is referred to as a NORD process.

If the patient is willing and able to pay at 230, the patient is informed of the cost of the product and is given payment options at 234. At 236, once payment is received, the intake reimbursement specialist submits a coverage approval form with the enrollment form to the pharmacy team as notification to process the patient's prescription. If coverage is approved at 228, the intake reimbursement specialist also submits the coverage approval form with the enrollment form to the pharmacy team as notification to process the patient's prescription. Processing of the prescription is described below.

Upon receipt and initial processing of the prescription enrollment form and sending an original to the pharmacy work flow block 208, the patient is shipped a Xyrem® success packet via mail. In one embodiment, the Xyrem® success packet contains educational material for a patient that advises of the proper use, care and handling of the drug and consequences of diversion at 268. The medical doctor's credentials are checked to determine if the physician has a current DEA license to prescribe controlled substances and if he or she has had any actions related to misuse/misprescribing of controlled drugs against him or her, within a predetermined time, such as three months at 270. If they have, a pharmacist holds the prescription until receiving a coverage approval form from the intake reimbursement specialist at 272.

If the credentials have not been recently checked, the pharmacist verifies the credentials and enters all findings in the database at 274. If the credentials are approved at 276, the physician is indicated as approved in a physician screen populated by information from the database at 280. The prescription is then held pending coverage approval at 282.

If any disciplinary actions are identified, as referenced at block 278, management of the pharmacy is notified and either approves processing of the prescription with continued monitoring of the physician, or processing of the prescription is not performed, and the physician is noted in the database as unapproved at 284. The enrollment form is then mailed back to the physician with a cover letter reiterating that the prescription cannot be processed at 288. The patient is also sent a letter at 290 indicating that the prescription cannot be processed and the patient is instructed to contact their physician.

Actual filling of the approved prescription begins with receipt of the coverage approval form as indicated at 240. The patient is contacted by the pharmacy, such as by a technician to complete a technician section of a patient counseling checklist. If a pharmacist verifies that the program materials were not read at 242, the receipt of the material is confirmed at 244 and another call is scheduled to counsel the patient before the drug is shipped.

If the program materials, were read at 242, the checklist is completed at 246 and the technician transfers the patient to the pharmacist who reviews the entire checklist and completes remaining pharmacist specified sections. At 248, the pharmacists indicates in the database that the patient counseling and checklist was successfully completed, indicating the date completed.

At 250, the pharmacist schedules the patient's shipment for the next business day or the next business day that the patient or designee is able to sign for the package. Further, as indicated at 252, the shipment must be sent to the patient's home address unless the patient is traveling or has moved. In that event, the pharmacist may determine that an exception may be made. The patient or the patient's designee who is at least 18 years old, must sign for the package upon delivery.

At 254, the pharmacist enters the prescription order in the database, creating an order number. The pharmacist then verifies at 256 the prescription and attaches a verification label to the hard copy prescription. At 258, a pick ticket is generated for the order and the order is forwarded to the pharmacy for fulfillment. The shipment is confirmed in the database at 260, and the order is shipped by USPS Express Mail. Use of the US mail invokes certain criminal penalties for unauthorized diversion. Optionally, other mail services may be used. Potential changes in the law may also bring criminal penalties into play. Following shipment, the patient is called by the central pharmacy to confirm that the prescription was received.

As noted at 266, for the sensitive drug, Xyrem, all inventory is cycle counted and reconciled with the database system quantities before shipments for the day are sent. This provides a very precise control of the inventory.

Figure 3:
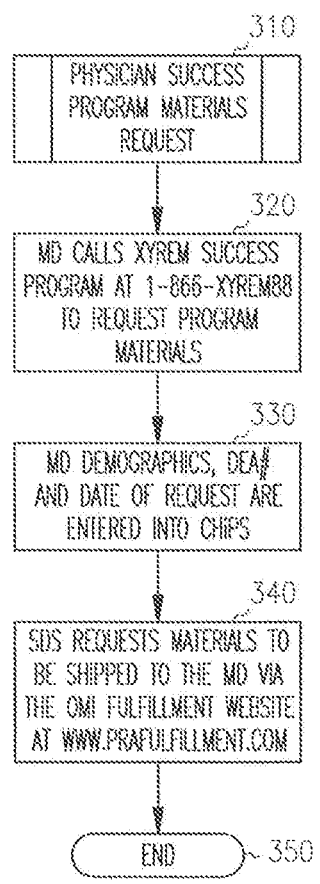
FIG. 3 is a flowchart of a physician success program at least partially implemented on a computer system such as that shown in FIG. 1.

A physician success program materials request process begins at 310 in FIG. 3. At 320, the MD calls to the central pharmacy to request program materials. A special phone number is provided. MD demographics, DEA number, and data or request are entered into the database at 330. At 340, a request is made to ship the materials to the MD via a fulfillment website, or other mechanism. The request process ends at 350.

Figure 4A:
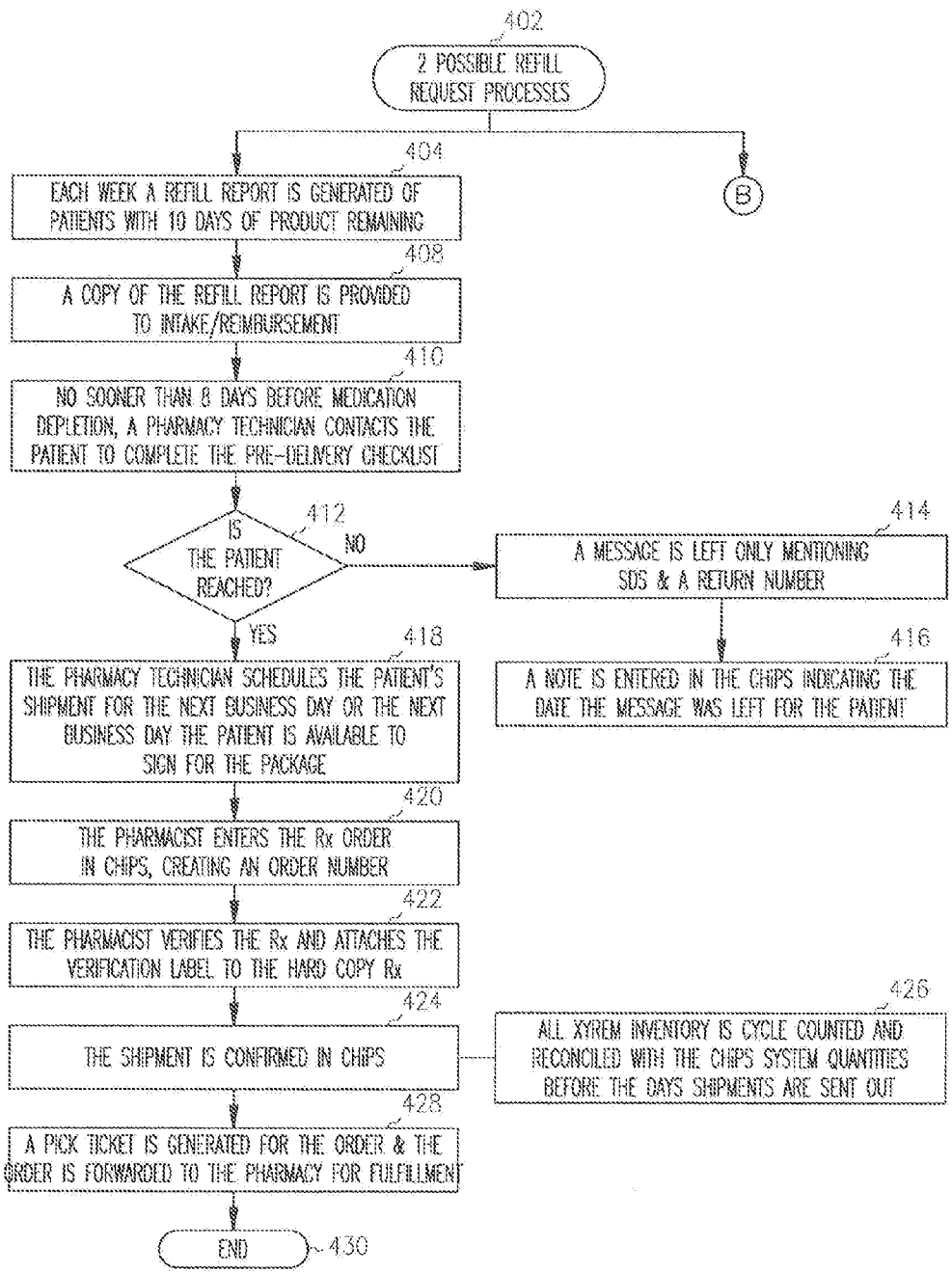
FIGS. 4A and 4B are a flowchart describing a method for handling refill requests at least partially utilizing a computer system such as that shown in FIG. 1.
Figure 4B:
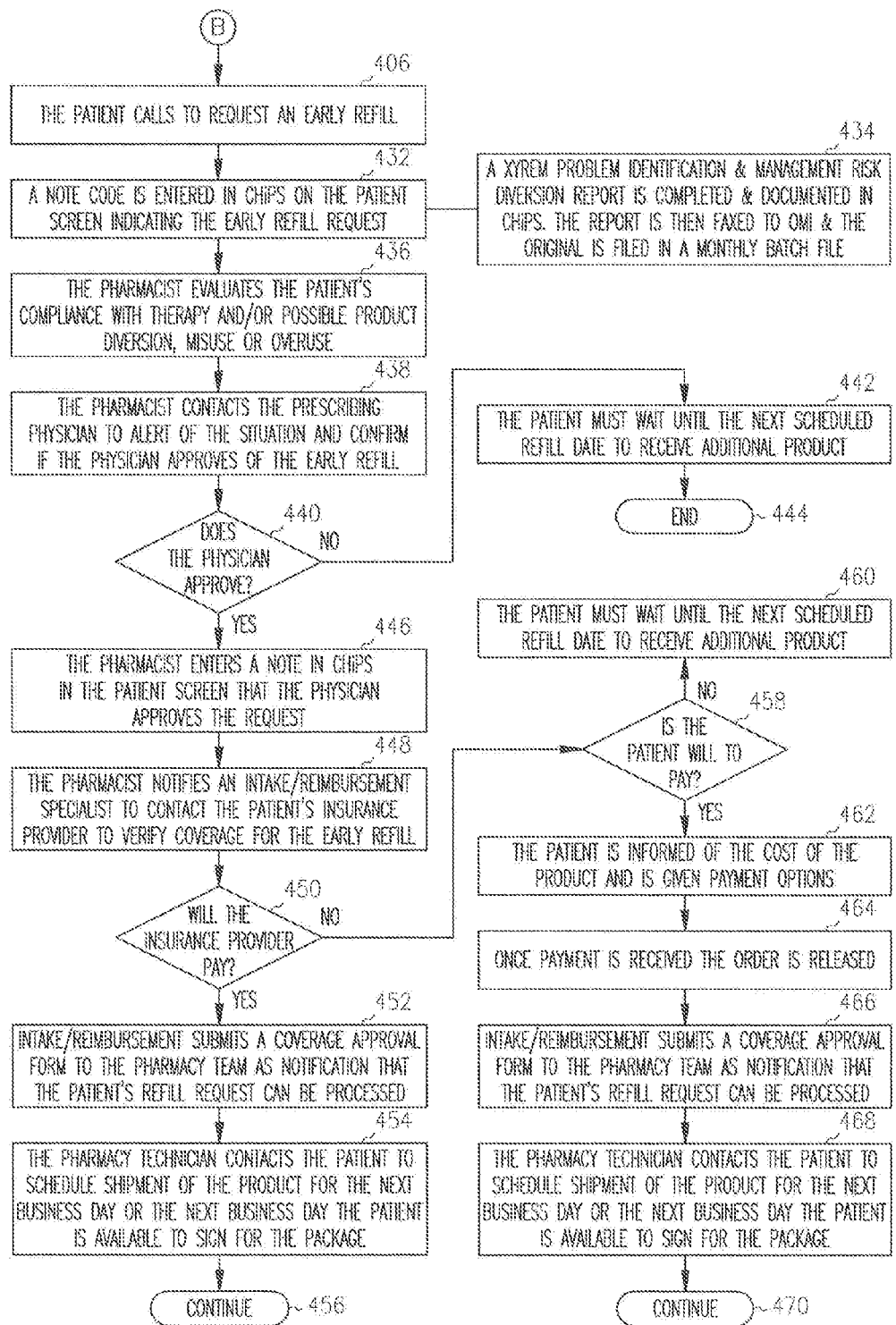
Figure 5:
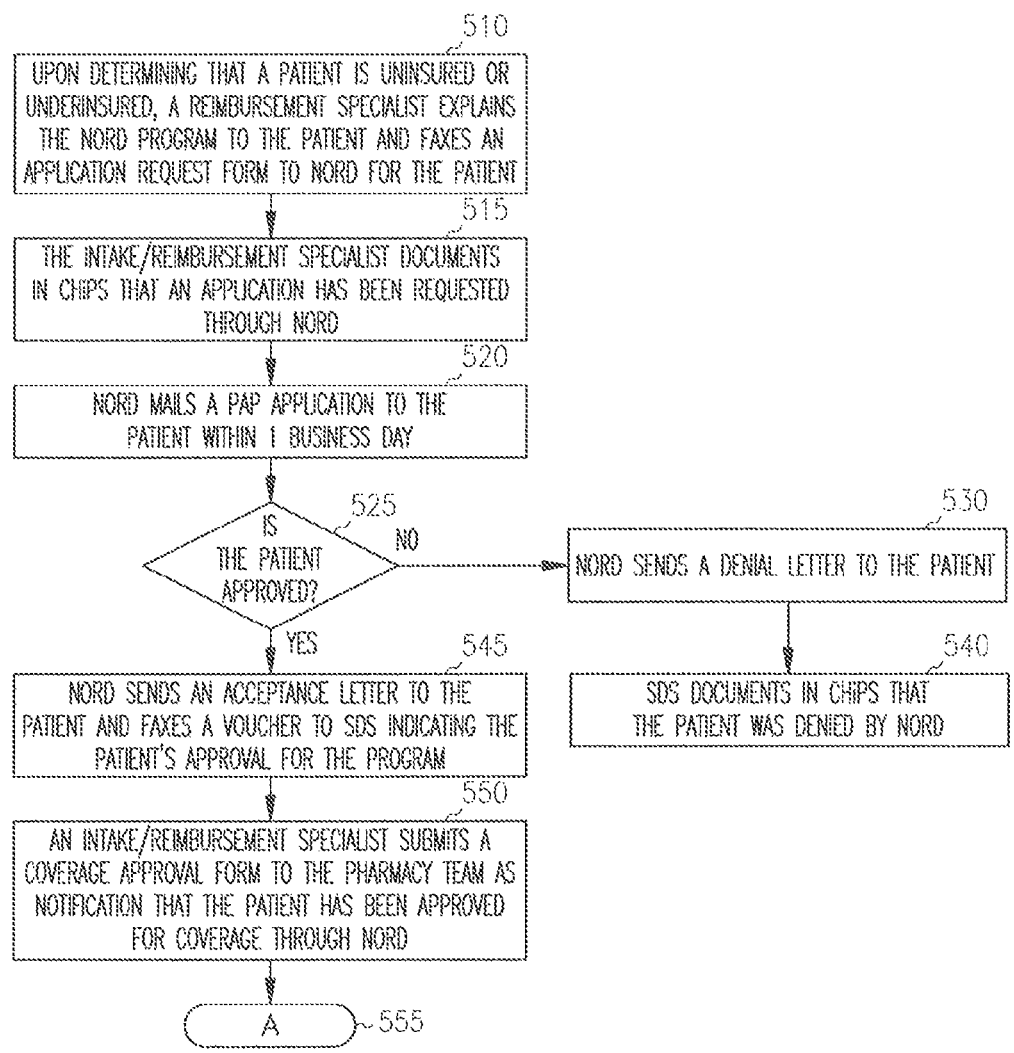
FIG. 5 is a flowchart of a process for requesting special reimbursement when a patient is uninsured or underinsured at least partially utilizing a computer system as that shown in FIG. 1.

A refill request process begins at 302 in FIGS. 4A and 4B. There are two different paths for refills. A first path beginning at 404 involves generating a report from the central database of patients with a predetermined number of days or product remaining. A second path beginning at 406 is followed when a patient calls to request an early refill.

In the first path, a copy of the report is provided to an intake reimbursement specialist at 408. No sooner than 8 days before the medication depletion, a pharmacy technician contacts the patient at 410 to complete the pre-delivery 30 checklist. At 412, if the patient is not reached, a message is left mentioning the depletion, and a return number at 414. A note is also entered into the database indicating the date the message was left at 416.

If the patient is reached at 412, the next shipment is scheduled at 418, the prescription is entered into the database creating an order at 420, the pharmacist verifies the prescription and attaches a verification label at 422 and the shipment is confirmed in the database at 424. Note at 426 that the inventory is cycle counted and reconciled with the database quantities before the shipments for a day or other time period are sent. A pick ticket is generated for the order and the order is forwarded for fulfillment at 428, with the first path ending at 430.

The second path, beginning at 406 results in a note code being entered into the database on a patient screen indicating an early refill request at 432. The pharmacist evaluates the patient's compliance with therapy or possible product diversion, misuse or over-use at 436. In one embodiment, cash payers are also identified. The pharmacist then contacts the prescribing physician to alert them of the situation and confirm if the physician approves of the early refill at 438. If the physician does not approve as indicated at 440, the patient must wait until the next scheduled refill date to receive additional product as indicated at 442, and the process ends at 444.

If the physician approves at 440, the pharmacist enters a note in the database on a patient screen that the physician approves the request at 446. The pharmacist notifies an intake reimbursement specialist to contact the patient's insurance provider to verify coverage for the early refill at 448. If the insurance provider will pay as determined at 450, the specialist submits the coverage approval form as notification that the refill may be processed at 452. At 454, the pharmacy technician contacts the patient to schedule shipment of the product for the next business day, and the process of filling the order is continued at 456 by following the process beginning at 240.

If the insurance provider will not pay at 450, it is determined whether the patient is willing and/or able to pay at 458. If not, the patient must wait until the next scheduled refill date to receive additional product at 460. If it was determined at 458 that the patient was willing and able to pay, the patient is informed of the cost of the product and is given payment options at 462. Once payment is received as indicated at 464, the specialist submits a coverage approval form to the pharmacy team as notification that the refill request can be processed at 466. At 468, the pharmacy technician contacts the patient to schedule shipment. The process of filling the order is continued at 470 by following the process beginning at 240.

A process, referred to as a NORD process in one embodiment is used to determine whether donated, third party funds are available for paying for prescriptions where neither insurance will, nor the patient can pay. The process begins at 510 upon determining that a patient is uninsured or underinsured. A reimbursement specialist explains the NORD program to the patient and faxes an application request form to NORD for the patient. At 515, the intake reimbursement specialist documents in the database that an application has been received through NORD. At 520, NORD mails an application to the patient within one business day.

A determination is made at 525 by NORD whether the patient is approved. If not, at 530, NORD sends a denial letter to the patient, and it is documented in the database at 540 that the patient was denied by NORD. If the patient is approved, NORD sends an acceptance letter to the patient and faxes a voucher to the central pharmacy (SDS in one embodiment) to indicate the approval at 545. At 550, an intake reimbursement specialist submits a coverage approval form to the pharmacy team as notification that the patient has been approved for coverage. The process of filling the order is continued at 555 by following the process beginning at 240.

An inventory control process is illustrated in FIG. 6 beginning at 610. Each week, a responsible person at the central pharmacy, such as the director of the pharmacy transfers inventory for the week's shipments to a segregated warehouse location for production inventory. At 620, a purchase order is generated for the inventory transferred to the production location and is sent, such as by fax, to a controller, such as the controller of the company that obtained approval for distribution and use of the sensitive drug. At 630, the controller invoices the central pharmacy for the product moved to production. The process ends at 640.

The central database described above is a relational database running on the system of FIG. 1, or a server based system having a similar architecture coupled to workstations via a network, as represented by communications 160. The database is likely stored in storage 140, and contains multiple fields of information as indicated at 700 in FIG. 7. The organization and groupings of the fields are shown in one format for convenience. It is recognized that many different organizations or schemas may be utilized. In one embodiment, the groups of fields comprise prescriber fields 710, patient fields 720, prescription fields 730 and insurance fields 740. For purposes of illustration, all the entries described with respect to the above processes are included in the fields. In further embodiments, no such groupings are made, and the data is organized in a different manner.

Several queries are illustrated at 800 in FIG. 8. There may be many other queries as required by individual state reporting requirements. A first query at 810 is used to identify prescriptions written by physician. The queries may be written in structured query language, natural query languages or in any other manner compatible with the database. A second query 820 is used to pull information from the database related to prescriptions by patient name. A third query 830 is used to determine prescriptions by frequency, and a $n^{th}$ query finds prescriptions by dose at 840. Using query languages combined with the depth of data in the central database allows many other methods of investigating for potential abuse of the drugs. The central database ensures that all prescriptions, prescribers and patients are tracked and subject to such investigations. In further embodiments, the central database may be distributed among multiple computers provided a query operates over all data relating to such prescriptions, prescribers and patients for the drug.

An example of one prescription and enrollment form is shown at 900 in FIG. 9. As previously indicated, several fields are included for prescriber information, prescription information and patient information.

Figure 10:
FIG. 10 is a copy of one example of a NORD application request form for patient financial assistance.

FIG. 10 is a copy of one example NORD application request form 1000 used to request that an application be sent to a patient for financial assistance.

FIG. 11 is a copy of one example application 1100 for financial assistance as requested by form 1000. The form requires both patient and physician information. Social security number information is also requested. The form provides information for approving the financial assistance and for tracking assistance provided.

FIG. 12 is a copy of one example voucher request for medication for use with the NORD application request form of FIG. 10. In addition to patient and physician information, prescription information and diagnosis information is also provided.

FIGS. 13A, 13B and 13C are descriptions of sample reports obtained by querying a central database having fields represented in FIG. 7. The activities grouped by sales, regulatory, quality assurance, call center, pharmacy, inventory, reimbursement, patient care and drug information. Each report has an associated frequency or frequencies. The reports are obtained by running queries against the database, with the queries written in one of many query languages.

While the invention has been described with respect to a Schedule III drug, it is useful for other sensitive drugs that are DEA or Federally scheduled drugs in Schedule II-V, as well as still other sensitive drugs where multiple controls are desired for distribution and use.

The invention claimed is:

1. A computer-implemented system for treatment of a narcoleptic patient with a prescription drug that has a potential for misuse, abuse or diversion, comprising:
   one or more computer memories for storing a single computer database having a database schema that contains and interrelates prescription fields, patient fields, and prescriber fields;
   said prescription fields, contained within the database schema, storing prescriptions for the prescription drug with the potential for abuse, misuse or diversion, wherein the prescription drug is sold or distributed by a company that obtained approval for distribution of the prescription drug;
   said patient fields, contained within the database schema, storing information sufficient to identify the narcoleptic patient for whom the company's prescription drug is prescribed;
   said prescriber fields, contained within the database schema, storing information sufficient to identify a physician or other prescriber of the company's prescription drug and information to show that the physician or other prescriber is authorized to prescribe the company's prescription drug;
   a data processor configured to:
   process a database query that operates over all data related to the prescription fields, prescriber fields, and patient fields for the prescription drug; and
   reconcile inventory of the prescription drug before the shipments for a day or other time period are sent by using said database query to identify information in the prescription fields and patient fields;

wherein the data processor is configured to process a second database query that identifies that the narcoleptic patient is a cash payer and a physician that is interrelated with the narcoleptic patient through the schema of the single computer database;

said identifying that the narcoleptic patient is a cash payer by said second database query being an indicator of a potential misuse, abuse or diversion by the narcoleptic patient and being used to notify the physician that is interrelated with the narcoleptic patient through the schema of the single computer database.

2. The system of claim 1, wherein the data processor selectively blocks shipment of the prescription drug to the patient based upon said identifying by the database query.

3. The system of claim 1, wherein the prescription drug is shipped to the narcoleptic patient if no potential misuse, abuse or diversion is found for the narcoleptic patient.

4. The system of claim 1, wherein the single computer database is an exclusive database that receives data associated with all patients being prescribed the prescription drug that is associated with the company.

5. The system of claim 1, wherein an exclusive central pharmacy controls the single computer database.

6. The system of claim 1 wherein the prescription drug comprises gamma hydroxyl butyrate (GHB).

7. The system of claim 1, wherein the single computer database comprises a relational database.

8. The system of claim 1, wherein the single computer database is distributed among multiple computers and the database query operates over all data relating to said prescription fields, prescriber fields, and patient fields for the prescription drug.

9. The system of claim 1, wherein the data processor is configured to initiate an inquiry to a prescriber when one or more prescription fields, patient fields, or prescriber fields are incomplete in the computer database.

10. The system of claim 1, wherein the data processor is configured to process a third database query that identifies an expected date for a refill of the prescription drug.

11. The system of claim 10, wherein the expected date is based on a prescription for the prescription drug and a date of a previous filling of the prescription.

12. The system of claim 11, wherein the prescription identifies an amount of the prescription drug to be provided and a schedule for consumption of the prescription drug.

13. The system of claim 1, wherein the database schema further contains and interrelates insurance fields, wherein the insurance fields, contained within the database schema, store information sufficient to identify an insurer to be contacted for payment for prescription drugs of an associated patient.

14. The system of claim 1, wherein the single computer database is used to identify a current pattern or an anticipated pattern of abuse of the prescription drug; wherein the current pattern or the anticipated pattern are identified using periodic reports generated from the single computer database.

15. The system of claim 14, wherein one or more controls for distribution of the prescription drug are selected based on the identified pattern.

16. The system of claim 15, wherein the one or more controls are submitted to an approval body for approval of distribution of the prescription drug.

17. The system of claim 1, wherein additional controls for distribution are selected in a negotiation with an approval body to garner the approval of distribution.

18. The system of claim 17, wherein the data processor is used to add further controls until approval is obtained.

19. The system of claim 18, wherein the approval body is the Food and Drug Administration (FDA) or the Drug Enforcement Agency (DEA).

20. The system of claim 1, wherein current inventory is cycle counted and reconciled with database quantities before shipments for a day or other time period are sent.

21. The system of claim 1, wherein the single computer database comprises an exclusive computer database of the company that obtained approval for distribution of the prescription drug, wherein all prescriptions for the company's prescription drug are stored only in the exclusive computer database of the company, and wherein the company's prescription drug is sold or distributed by the company using only the exclusive computer database of the company.

22. The system of claim 1, wherein the single computer database comprises a single computer database of the company that obtained approval for distribution of the prescription drug, wherein the prescription fields store all prescription requests, for all patients being prescribed the company's prescription drug, only in the single computer database of the company, from all physicians or other prescribers allowed to prescribe the company's prescription drug, such that all prescriptions for the company's prescription drug are processed using only the single computer database of the company.

23. A computer-implemented system for treatment of a narcoleptic patient with a prescription drug that has a potential for misuse, abuse or diversion, comprising:

one or more computer memories for storing a single computer database having a database schema that contains and interrelates prescription fields, patient fields, and prescriber fields;

said prescription fields, contained within the database schema, storing prescriptions for the prescription drug with the potential for abuse, misuse or diversion, wherein the prescription drug is sold or distributed by a company that obtained approval for distribution of the prescription drug;

said patient fields, contained within the database schema, storing information sufficient to identify the narcoleptic patient for whom the company's prescription drug is prescribed;

said prescriber fields, contained within the database schema, storing information sufficient to identify a physician or other prescriber of the company's prescription drug and information to show that the physician or other prescriber is authorized to prescribe the company's prescription drug;

a data processor for processing a database query that operates over all data related to the prescription fields, prescriber fields, and patient fields for the prescription drug;

said database query identifying information in the prescription fields and patient fields for reconciling inventory of the prescription drug before the shipments for a day or other time period are sent, wherein an inventory reconciliation is performed where current inventory is counted and reconciled with database quantities before shipments for a day or other time period are sent, and wherein the data processor is configured to selectively block shipment of the prescription drug based on the inventory reconciliation;

wherein the data processor is configured to process a second database query that identifies that the narcoleptic patient is a cash payer and a physician that is interrelated with the narcoleptic patient through the schema of the single computer database;

said identifying that the narcoleptic patient is a cash payer by said second database query being an indicator of a potential misuse, abuse or diversion by the narcoleptic patient and being used to notify the physician that is interrelated with the narcoleptic patient through the schema of the single computer database.

24. A computer-implemented system for treatment of a narcoleptic patient with a prescription drug that has a potential for misuse, abuse or diversion, wherein the prescription drug is sold or distributed by a company that obtained approval for distribution of the prescription drug, comprising:

one or more computer memories for storing a central computer database of the company that obtained approval for distribution of the prescription drug, for receiving prescriptions from any and all patients being prescribed the company's prescription drug, said central computer database having a database schema that contains and interrelates prescription fields, patient fields, and prescriber fields;

said central computer database being distributed over multiple computers;

said prescription fields, contained within the database schema, storing prescriptions for the prescription drug with the potential for abuse, misuse or diversion;

said patient fields, contained within the database schema, storing information sufficient to identify the narcoleptic patient for whom the company's prescription drug is prescribed;

said prescriber fields, contained within the database schema, storing information sufficient to identify any and all physicians or other prescribers of the company's prescription drug and information to show that the physicians or other prescribers are authorized to prescribe the company's prescription drug;

one or more data processors for processing one or more database queries that operate over data related to the prescription fields, prescriber fields, and patient fields for the prescription drug;

said one or more database queries checking for abuse within the central computer database, wherein the filling of the prescriptions is authorized for the company's prescription drug only if there is no record of incidents that indicate abuse, misuse, or diversion by the narcoleptic patient and prescriber and if there is a record of such incidents, the central computer database indicates that such incidents have been investigated, and the central computer database indicates that such incidents do not involve abuse, misuse or diversion.

25. The system of claim 24, wherein the one or more database queries are processed by the one or more data processors for identifying: that the narcoleptic patient is a cash payer and a physician that is interrelated with the narcoleptic patient through the schema of the single computer database;

said identifying that the narcoleptic patient is a cash payer by said second database query being an indicator of a potential misuse, abuse or diversion by the narcoleptic patient and being used to notify the physician that is interrelated with the narcoleptic patient through the schema of the single computer database.

26. The system of claim 24, where the central computer database is distributed among multiple computers, and where the one or more database queries operate over all data relating to said prescription fields, prescriber fields, and patient fields for the prescription drug.

27. The system of claim 24, wherein the central computer database is used to identify a current pattern or an anticipated pattern of abuse of the prescription drug;

wherein the current pattern or the anticipated pattern are identified using periodic reports generated from the single computer database.

28. The system of claim 24, wherein current inventory is cycle counted and reconciled with database quantities before shipments for a day or other time period are sent.

* * * * *

UNITED STATES PATENT AND TRADEMARK OFFICE
CERTIFICATE OF CORRECTION

| | | |
|---|---|---|
| PATENT NO. | : 8,731,963 B1 | Page 1 of 2 |
| APPLICATION NO. | : 13/592202 | |
| DATED | : May 20, 2014 | |
| INVENTOR(S) | : Reardan et al. | |

It is certified that error appears in the above-identified patent and that said Letters Patent is hereby corrected as shown below:

ON THE TITLE PAGE:

On page 2, in column 2, under "Other Publications", line 1, delete "mailed" and insert --filed--, therefor On page 2, in column 2, under "Other Publications", line 24, delete "mailed" and insert --filed--, therefor On page 2, in column 2, under "Other Publications", line 42, delete "mailed" and insert --filed--, therefor On page 2, in column 2, under "Other Publications", line 54, delete "mailed" and insert --filed--, therefor On page 3, in column 2, under "Other Publications", line 54, delete "Sodiium" and insert --Sodium--, therefor On page 3, in column 2, under "Other Publications", line 57, delete "Sodiium" and insert --Sodium--, therefor

IN THE DRAWINGS:

On sheet 9 of 16, Fig. 6, delete "236" and insert --610--, therefor

On sheet 9 of 16, Fig. 6, delete "236" and insert --612--, therefor

On sheet 9 of 16, Fig. 6, delete "236" and insert --630--, therefor

Signed and Sealed this
Eighteenth Day of November, 2014

Michelle K. Lee
*Deputy Director of the United States Patent and Trademark Office*

On sheet 9 of 16, Fig. 6, delete "350" and insert --640--, therefor

On sheet 12 of 16, Fig. 11, delete "XYREEM" and insert --XYREM--, therefor

IN THE SPECIFICATION:

In column 4, line 21, delete "RX/enrollment" and insert --Rx/enrollment--, therefor In column 6, line 16, delete "302" and insert --402--, therefor In column 6, line 25, after "pre-delivery", delete "30", therefor

IN THE CLAIMS:

In column 11, line 14, in Claim 24, after "drug,", insert --and--, therefor